US00PP27071P2

(12) United States Plant Patent
Hartman

(10) Patent No.: US PP27,071 P2
(45) Date of Patent: Aug. 16, 2016

(54) ***CALADIUM* PLANT NAMED 'BURNING HEART'**

(50) Latin Name: *Caladium×hortulanum*
Varietal Denomination: Burning Heart

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 104 days.

(21) Appl. No.: 14/544,175

(22) Filed: Dec. 4, 2014

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — June Hwu
(74) *Attorney, Agent, or Firm* — C. A. Whealy

(57) ABSTRACT

A new and distinct cultivar of *Caladium* plant named 'Burning Heart', characterized by its intermediate height, upright and uniform plant habit; vigorous growth habit; rapid growth rate; fancy-type leaves with upper leaf surface bronze in color with contrasting salmon orange-colored spots and lower leaf surface greyed green in color; and good landscape performance.

4 Drawing Sheets

Botanical designation: *Caladium×hortulanum.*
Cultivar denomination: 'BURNING HEART'.

BACKGROUND OF THE INVENTION

The present invention relates to a new and distinct cultivar of *Caladium* plant, botanically known as *Caladium×hortulanum*, commercially referred to as a fancy leaf-type *Caladium* and hereinafter referred to by the name 'Burning Heart'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2008 in Avon Park, Fla. of *Caladium×hortulanum* 'Red Flash', not patented, as the female, or seed, parent with *Caladium×hortulanum* 'Twist N Shout', not patented, as the male, or pollen, parent. The new *Caladium* plant was discovered and selected by the Inventor as a single plant within the progeny of the stated cross-pollination in a controlled outdoor nursery environment in Zolfo Springs, Fla. in September, 2009.

Asexual reproduction of the new *Caladium* plant by 'chipping' the tubers (cutting the tuber into segments with each segment containing an axillary bud and tuber cortical tissue) in a controlled outdoor nursery environment in Zolfo Springs, Fla. since April, 2010 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Burning Heart'. These characteristics in combination distinguish 'Burning Heart' as a new and distinct *Caladium* plant:

1. Intermediate in height, upright and uniform plant habit.
2. Vigorous growth habit and rapid growth rate.
3. Fancy-type leaves with upper leaf surface bronze in color with contrasting salmon orange-colored spots and lower leaf surface, greyed green in color.
4. Good landscape performance.

Plants of the new *Caladium* differ primarily from plants of the female parent, 'Red Flash', in the following characteristics:

1. Plants of the new *Caladium* are shorter than plants of 'Red Flash'.
2. Plants of the new *Caladium* are faster growing and produce finished plants about two to three weeks earlier than plants of 'Red Flash'.
3. Plants of the new *Caladium* and 'Red Flash' differ in leaf color as leaves of plants of 'Red Flash' are dark green in color with dark red-colored centers and primary veins and pink-colored spots.
4. Plants of the *Caladium* and 'Red Flash' differ in leaf petiole coloration as leaf petioles of plants of 'Red Flash' are red pink to tan pink in color with darker-colored stippling, stripes and tessellations.

Plants of the new *Caladium* differ primarily from plants of the male parent, 'Twist N Shout', in the following characteristics:

1. Plants of the new *Caladium* and 'Twist N Shout' differ in leaf shape and color as leaves of plants of 'Twist N Shout' are hastate in shape and olive green in color with coppery orange-colored blotches.
2. Plants of the *Caladium* and 'Twist N Shout' differ in leaf petiole coloration as leaf petioles of plants of 'Twist N Shout' are light green in color.

Plants of the new *Caladium* can be compared to plants of *Caladium×hortulanum* 'Postman Joyner', not patented. In side-by-side comparisons, plants of the new *Caladium* differed primarily from plants of 'Postman Joyner' in the following characteristics:

1. Plants of the new *Caladium* and 'Postman Joyner' differed in leaf color as leaves of plants of 'Postman Joyner' had red-colored centers with dark red-colored spots and dark green-colored margins.
2. Plants of the new *Caladium* and 'Postman Joyner' differed in leaf petiole color as leaf petioles of plants of 'Postman Joyner' were close to black in color.

Plants of the new *Caladium* can also be compared to plants of *Caladium×hortulanum* 'Frieda Hemple', not patented. In side-by-side comparisons, plants of the new *Caladium* differed primarily from plants of 'Frieda Hemple' in the following characteristics:

1. Plants of the new *Caladium* and 'Frieda Hemple' differed in leaf color as leaves of plants of 'Frieda Hemple' had red-colored centers and dark green-colored margins.
2. Plants of the new *Caladium* and 'Frieda Hemple' differed in leaf petiole color as leaf petioles of plants of 'Frieda Hemple' were tan pink in color with dense blackish brown-colored stippling and streaks.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Burning Heart' in a container and grown in a shadehouse (tuber not de-eyed).

The photograph at the top of the second sheet is a comparison view of typical potted plants of the female parent, 'Red Flash' (left), 'Burning Heart' (center) and the male parent, 'Twist N Shout' (right).

The photograph at the bottom of the second sheet is a comparison view of typical potted plants of 'Postman Joyner' (left), 'Burning Heart' (center) and 'Frieda Hemple' (right).

The photograph at the top of the third sheet is a comparison view of typical plants of 'Burning Heart' grown in containers; the plant on the left has not had its tuber de-eyed and the plant on the right has had its tuber de-eyed prior to planting.

The photograph at the bottom of the third sheet is a close-up view of typical freshly-harvested tubers and roots of 'Burning Heart' plants.

The photograph on the fourth sheet is a side perspective view of typical plants of 'Burning Heart' grown in an open field.

DETAILED BOTANICAL DESCRIPTION

The aforementioned photographs and following observations and measurements describe plants grown in 15-cm containers in a polypropylene-covered shadehouse (30% light reduction) in Avon Park, Fla. and plants grown in ground beds under full sunlight conditions in an outdoor nursery in Crewsville, Fla. The plants were grown under cultural practices typical of commercial shadehouse and outdoor nursery production. During the production of the shadehouse-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from about 10,000 to 12,000 foot-candles. Plants grown in the shadehouse were seven weeks old, and plants grown in the outdoor nursery were eight months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Burning Heart'.

Parentage:

*Female, or seed, parent.*—*Caladium×hortulanum* 'Red Flash', not patented.

*Male, or pollen, parent.*—*Caladium×hortulanum* 'Twist N Shout', not patented.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented and somewhat flattened; individual segments elliptic to ovate in shape. Height: About 3 cm. Diameter: About 4.3 cm. Segment height: About 1 cm. Segment diameter: About 1.2 cm. Texture: Thick, starchy; somewhat brittle. Color: Epidermis, freshly-harvested: Close to 199C. Epidermis, dried: Close to 200A. Cortical tissue: Close to 4D. Axillary buds: Close to N170D. Root description: Thick, fleshy contractile roots; color, close to 155C and 199A. Rooting habit: Sparse to medium density.

Plant description:

*Plant type.*—Herbaceous perennial; suitable as a potted plant in containers 15-cm to 25-cm and suitable as a landscape plant in shaded areas.

*Plant and growth habit.*—Intermediate in height, upright and uniformly mounded plant habit; vigorous and dense growth habit; rapid growth rate, potted plants in finished or saleable form in about six to seven weeks after planting tubers; leaf petioles and leaves arise from one or more growing points on tubers; petioles mostly upright and leaning outwardly with development.

*Plant height, from soil level to top of foliar plane, shadehouse-grown potted plants.*—About 34 cm to 40 cm.

*Plant diameter or spread, shadehouse-grown potted plants.*—About 46 cm to 50 cm.

*Number of shoots per plant, shadehouse-grown potted plants, tubers not de-eyed.*—About three develop per #1 tuber.

*Number of shoots per plant, shadehouse-grown potted plants, tubers de-eyed.*—About four to five develop per #1 tuber.

*Cataphylls, shadehouse-grown potted plants.*—Length: About 5 cm to 8 cm. Width: About 1 cm to 2 cm. Shape: Wedge-shaped. Apex: Acute. Base: Sheathing the stem. Color, inner surface: Close to 194D; colors and patterns of the outside surface are visible on the inner surface. Color, outer surface: Close to 195C and variably flushed with close to 182D; stippled, streaked and tessellated with close to between 199A and 200C; with development, color becoming closer to 199A to 199B and N199B, and stained with close to 187B to 187C.

Leaf description:

*Arrangement and type*.—Alternate; simple; fancy-type.

*Length, shadehouse-grown potted plants*.—About 21 cm to 30 cm.

*Width, shadehouse-grown potted plants, flattened*.—About 12 cm to 18 cm.

*Shape*.—Ovate.

*Apex*.—Acute to acuminate.

*Base*.—Sagittate to peltate.

*Margin*.—Entire; flat to somewhat wavy with broad undulations.

*Texture, upper and lower surfaces*.—Smooth, glabrous.

*Luster, upper surface*.—Somewhat metallic.

*Luster, lower surface*.—Dull.

*Venation pattern*.—Pinnate.

*Color, shadehouse-grown potted plants*.—Developing and fully expanded leaves, upper surface: Main colors: Ground color close to N189A tinged with close to 147A; heavily overlaying with close to darker than 183A; areas surrounding venation, darker than and closest to 183A. Margins: Close to 187A tinged with close to 183A. Basal notch: Close to 187A to 187B tinged with close to 183A. Midrib and primary venation: Close to 183A tinged with close to 187A and 53A. Random spots: Close to 48A. Developing and fully expanded leaves, lower surface: Main colors: Close to 195D tinged with close to 146B and faintly tinged with close to 187B; areas surrounding venation, close to 195D tinged with close to 183B. Margins: Close to 187A tinged with close to 183A. Basal notch: Close to 187A to 187B; line descending from basal notch, close to 187B. Midrib: Close to 195A to 195B. Primary venation: Close to 195A tinged with close to 146B. Random spots: Close to 181B, 181C, 181D or 191A.

*Petioles*.—Aspect: Initially upright and straight; with development, leaning outwardly; flexible. Length, shadehouse-grown potted plants: About 28 cm to 32 cm. Diameter, distal, shadehouse-grown potted plants: About 3.5 mm to 4 mm. Diameter, proximal, shadehouse-grown potted plants: About 6 mm to 9 mm. Texture: Smooth, glabrous; glaucous. Color, shadehouse-grown potted plants, Just below the leaf and petiole junction: Close to 195C or close to 195C tinged with close to 182D; variably and faintly stippled, streaked and tessellated with close to 199A. Overall: Close to 195C and variably flushed with close to 182D; faintly stippled, streaked and tessellated with close to 199A. Wing length, shadehouse-grown potted plants: About 6.5 cm to 12 cm. Wing diameter, shadehouse-grown potted plants: About 9 mm. Texture, inner and outer surfaces: Smooth, glabrous. Wing color, shadehouse-grown potted plants, inner surface: Close to 194D. Wing color, shadehouse-grown potted plants, outer surface: Close to 195C, 195A or 147B variably tinged with close to N170D; stippled, streaked and tessellated with close to 199A and 199A tinged with close to 147B.

Inflorescence description: To date, inflorescence development has not been observed on shadehouse-grown potted plants nor on outdoor nursery-grown plants.

Disease & pest tolerance: Plants of the new *Caladium* have been observed to have above average tolerance to *Xanthomonas* Leaf Spot and to have average tolerance to *Pythium* Root Rot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11.

It is claimed:

1. A new and distinct *Caladium* plant named 'Burning Heart' as illustrated and described.

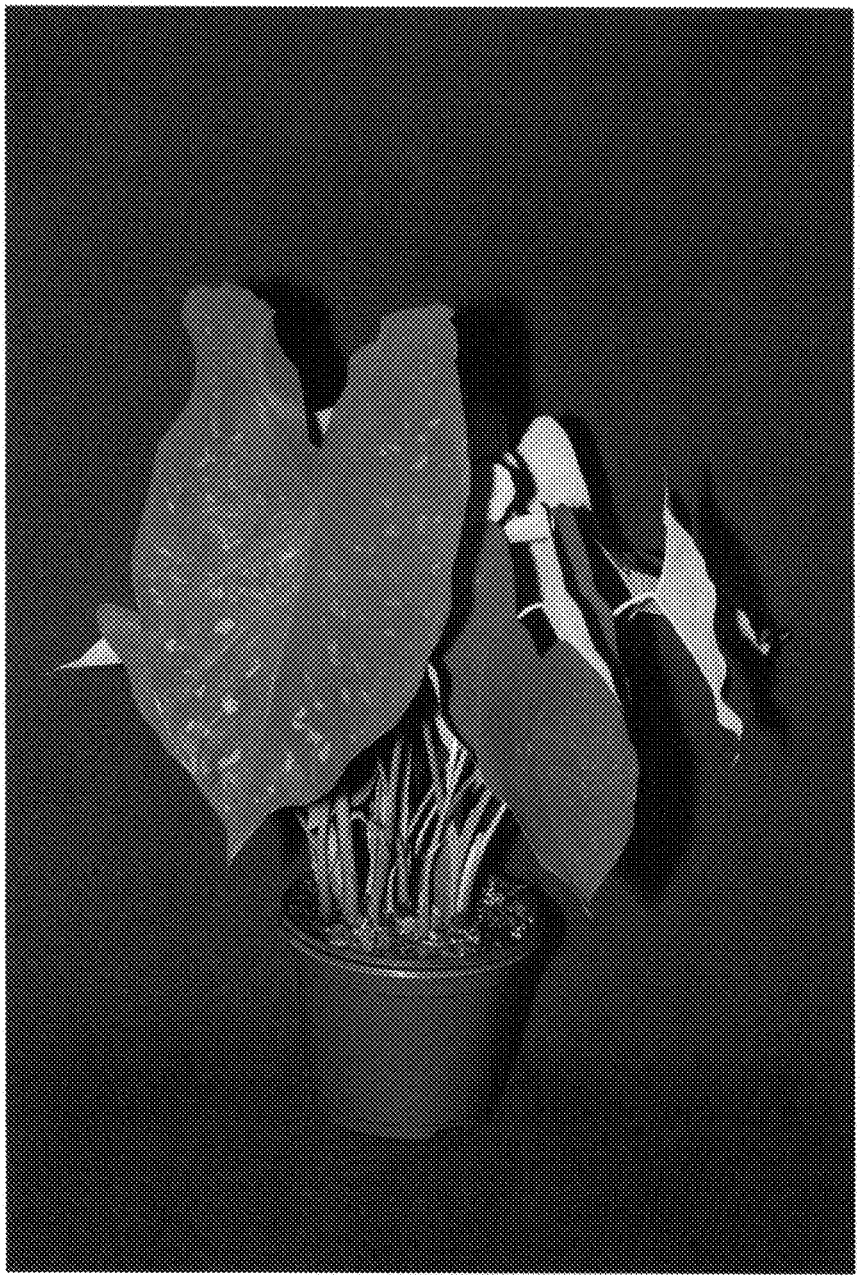

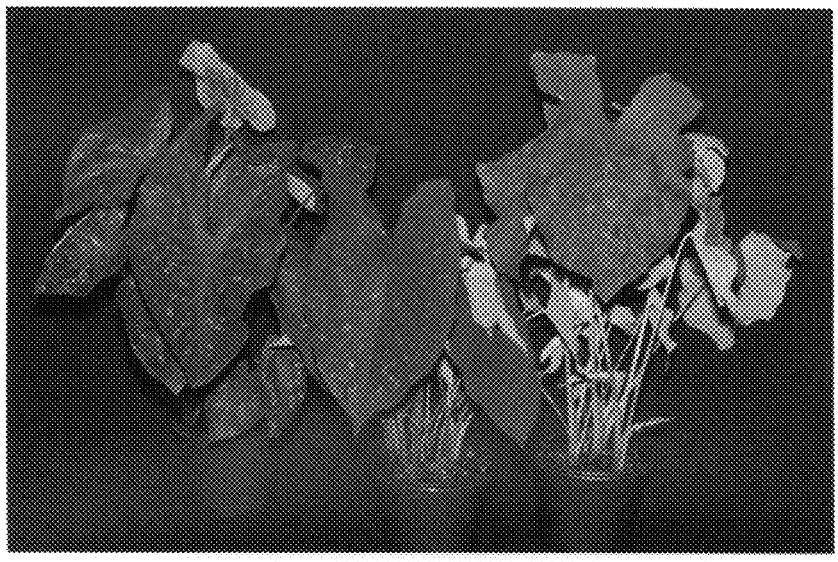
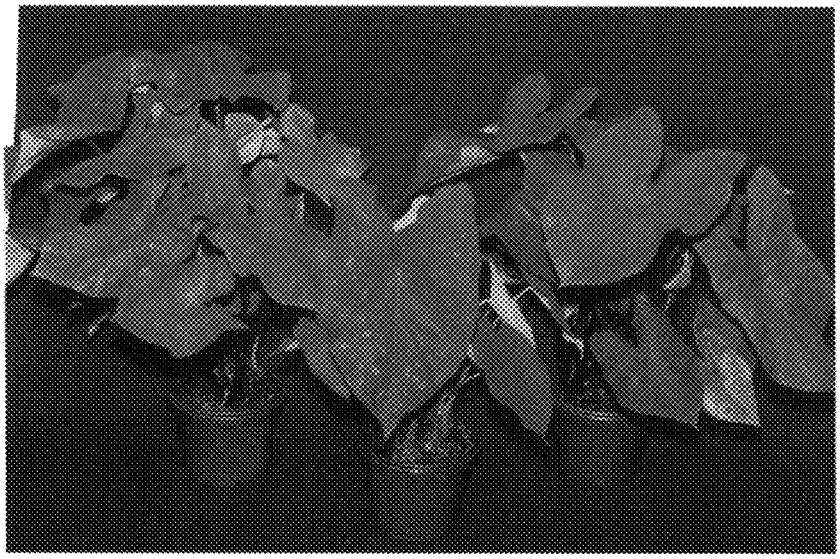

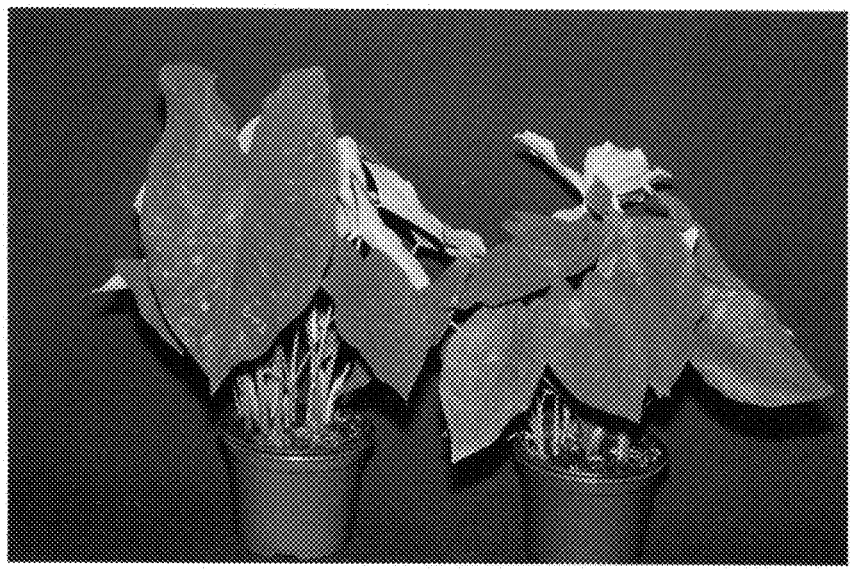
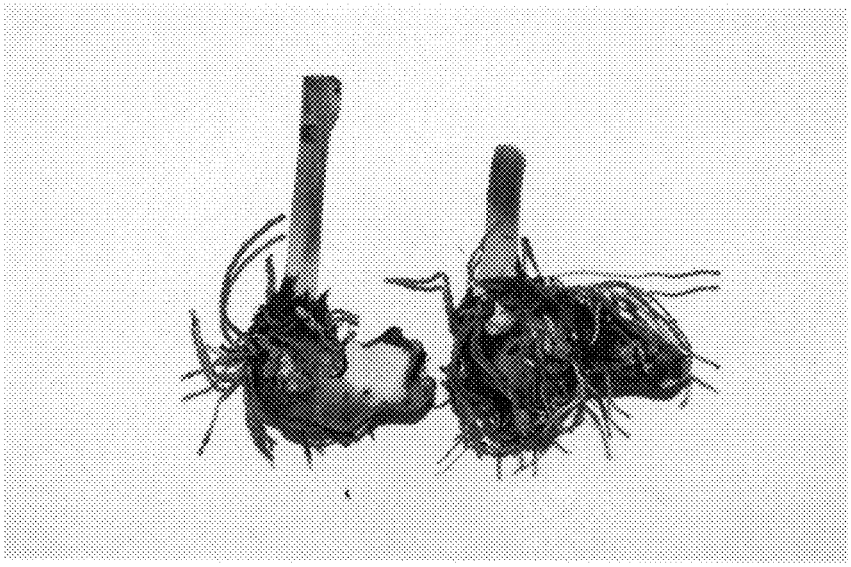

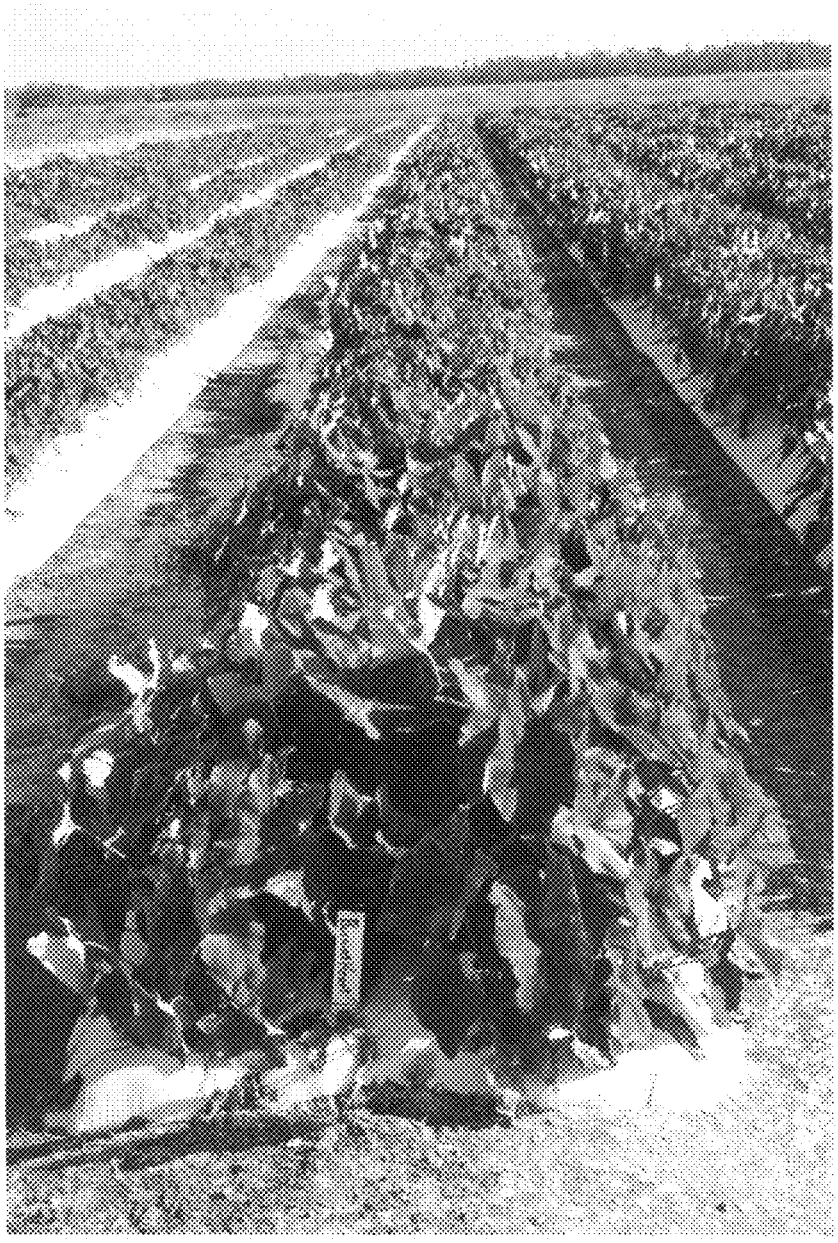

* * * * *